(12) United States Patent
Sutherland et al.

(10) Patent No.: US 11,872,881 B2
(45) Date of Patent: Jan. 16, 2024

(54) MOBILE ROBOT

(71) Applicant: CROSSWING INC., Aurora (CA)

(72) Inventors: Stephen Sutherland, Aurora (CA);
Philippe Guillaumont, Oakville (CA);
Daniel Sutherland, Aurora (CA)

(73) Assignee: CrossWing Inc., Aurora (CA)

( * ) Notice: Subject to any disclaimer, the term of this patent is extended or adjusted under 35 U.S.C. 154(b) by 0 days.

(21) Appl. No.: 17/711,198

(22) Filed: Apr. 1, 2022

(65) Prior Publication Data

US 2022/0227226 A1 Jul. 21, 2022
US 2023/0148454 A9 May 11, 2023

Related U.S. Application Data

(63) Continuation of application No. 16/317,353, filed as application No. PCT/CA2017/000170 on Jul. 13, 2017, now Pat. No. 11,305,645.

(Continued)

(51) Int. Cl.
*B60K 17/14* (2006.01)
*A47L 9/00* (2006.01)
(Continued)

(52) U.S. Cl.
CPC .............. *B60K 17/14* (2013.01); *A47L 9/009* (2013.01); *A47L 9/2852* (2013.01); *A47L 9/30* (2013.01);
(Continued)

(58) Field of Classification Search
CPC .... B60K 17/14; B60K 17/043; B60K 17/356; B60K 1/04; B60K 7/0007; B60K 8/00; B60K 2001/0405; B60K 2007/0046; B60K 2007/0061; B60K 2007/0076; B60K 7/007; B60B 7/20; B60B 19/003; B60B 19/12; B25J 5/007; B62B 3/12; B62B 5/004; B62B 5/0069; B62D 61/06; B60Y 2200/80; B60Y 2300/08; B60Y 2400/30; A47L 11/4044; A47L 11/405; A47L 9/009; A47L 9/2852;
(Continued)

(56) References Cited

U.S. PATENT DOCUMENTS 3,016,966 A 1/1962 Hansen
9,014,848 B2 4/2015 Farlow et al.
(Continued)

FOREIGN PATENT DOCUMENTS

CN 104210572 A 12/2014
CN 204056041 U 12/2014

OTHER PUBLICATIONS

International Search Report issued on PCT/CA2017/000170, dated Jan. 18, 2018.

*Primary Examiner* — Kiet T Nguyen
(74) *Attorney, Agent, or Firm* — Laurie Wright; Christopher Hunter; Blake, Cassels & Graydon LLP

(57) ABSTRACT

The improved mobile robot utilizes a cooperative wheeled support arrangement having a unique axle design that preferably cooperates with a base support module. A tri-axle is preferably used to support at least one omni-wheel on each axle section. Multiple omni-wheels on each section can be used for higher load applications. The tri-axle is of a fixed design and each wheel pivots on the individual axle section. Preferably, the axle sections are welded to each other.

12 Claims, 18 Drawing Sheets

Related U.S. Application Data

(60) Provisional application No. 62/361,621, filed on Jul. 13, 2016.

(51) Int. Cl.

| | | |
|---|---|---|
| *A47L 9/28* | (2006.01) | |
| *A47L 9/30* | (2006.01) | |
| *A61L 2/10* | (2006.01) | |
| *A61L 2/26* | (2006.01) | |
| *B25J 5/00* | (2006.01) | |
| *B60B 7/20* | (2006.01) | |
| *B60B 19/00* | (2006.01) | |
| *B60B 19/12* | (2006.01) | |
| *B60K 7/00* | (2006.01) | |
| *B62B 3/12* | (2006.01) | |
| *B62B 5/00* | (2006.01) | |
| *B62D 61/06* | (2006.01) | |
| *B60K 17/356* | (2006.01) | |

(52) U.S. Cl.
CPC ................... *A61L 2/10* (2013.01); *A61L 2/26* (2013.01); *B25J 5/007* (2013.01); *B60B 7/20* (2013.01); *B60B 19/003* (2013.01); *B60B 19/12* (2013.01); *B60K 7/0007* (2013.01); *B60K 17/356* (2013.01); *B62B 3/12* (2013.01); *B62B 5/004* (2013.01); *B62B 5/0069* (2013.01); *B62D 61/06* (2013.01); *A47L 2201/04* (2013.01); *A61L 2202/11* (2013.01); *A61L 2202/16* (2013.01); *A61L 2202/17* (2013.01); *B60K 2007/0046* (2013.01); *B60K 2007/0076* (2013.01)

(58) Field of Classification Search
CPC .......... A47L 9/30; A47L 2201/04; A61L 2/10; A61L 2/26; A61L 2202/11; A61L 2202/16; A61L 2202/17
USPC ...................................................... 318/568.12
See application file for complete search history.

(56) References Cited

U.S. PATENT DOCUMENTS

| | | |
|---|---|---|
| 9,211,648 B2 | 12/2015 | Grinstead et al. |
| 2007/0150111 A1 | 6/2007 | Wu et al. |
| 2014/0009561 A1* | 1/2014 | Sutherland ............ H04N 7/185 |
| | | 348/14.05 |
| 2014/0110915 A1 | 4/2014 | Maeda |
| 2015/0190927 A1 | 7/2015 | Sutherland et al. |
| 2016/0291160 A1 | 10/2016 | Zweigle et al. |
| 2016/0309973 A1* | 10/2016 | Sheikh ................ A47L 11/4072 |
| 2016/0375337 A1* | 12/2016 | Kastner ............. H04M 1/72415 |
| | | 473/441 |

* cited by examiner

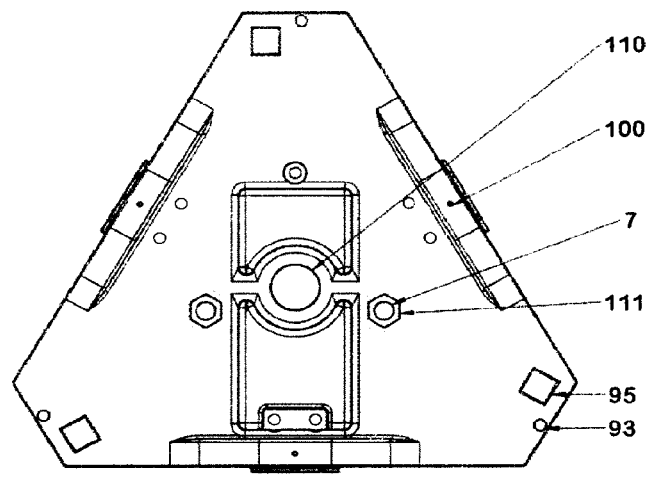
FIG. 11
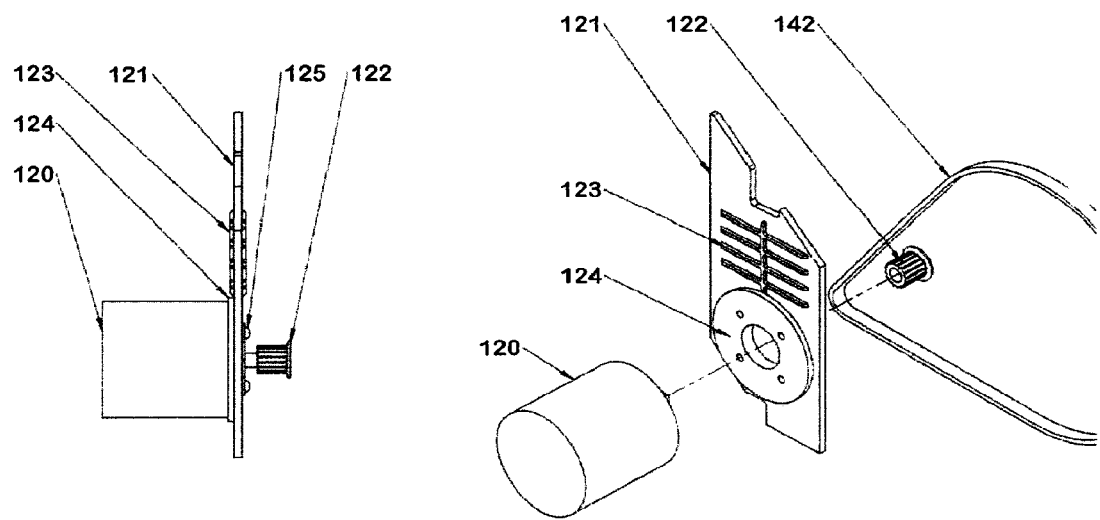
FIG. 12
FIG. 13

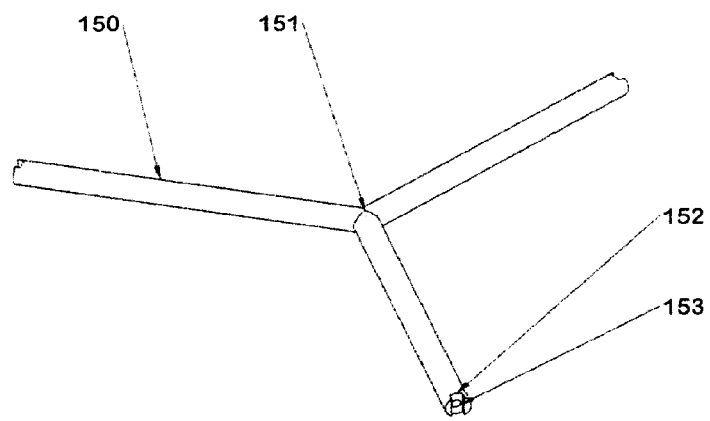
FIG. 15
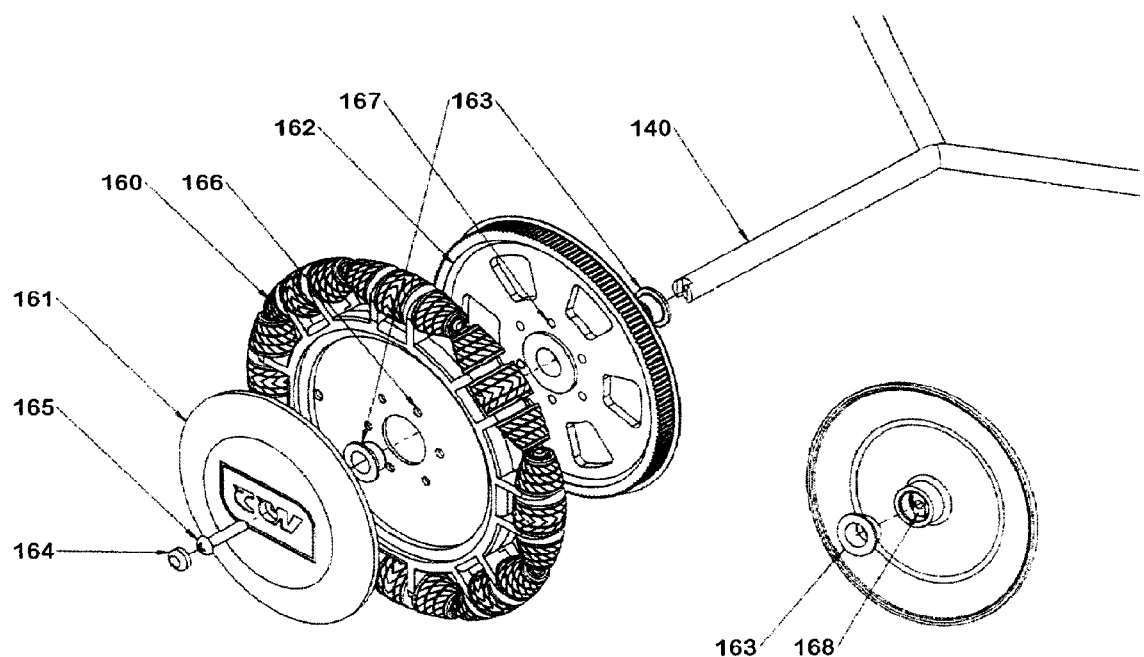
FIG. 16
FIG. 16B

FIG. 33
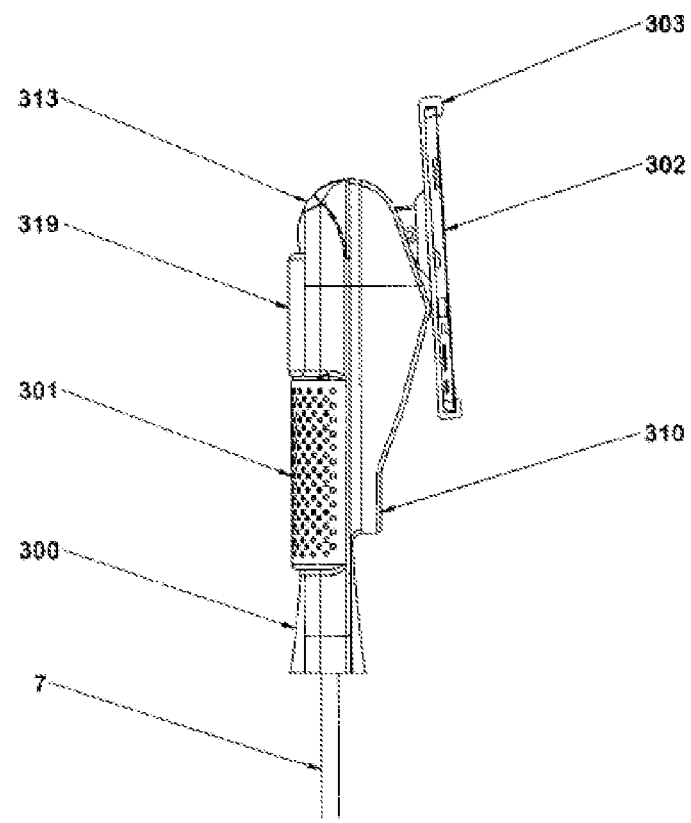
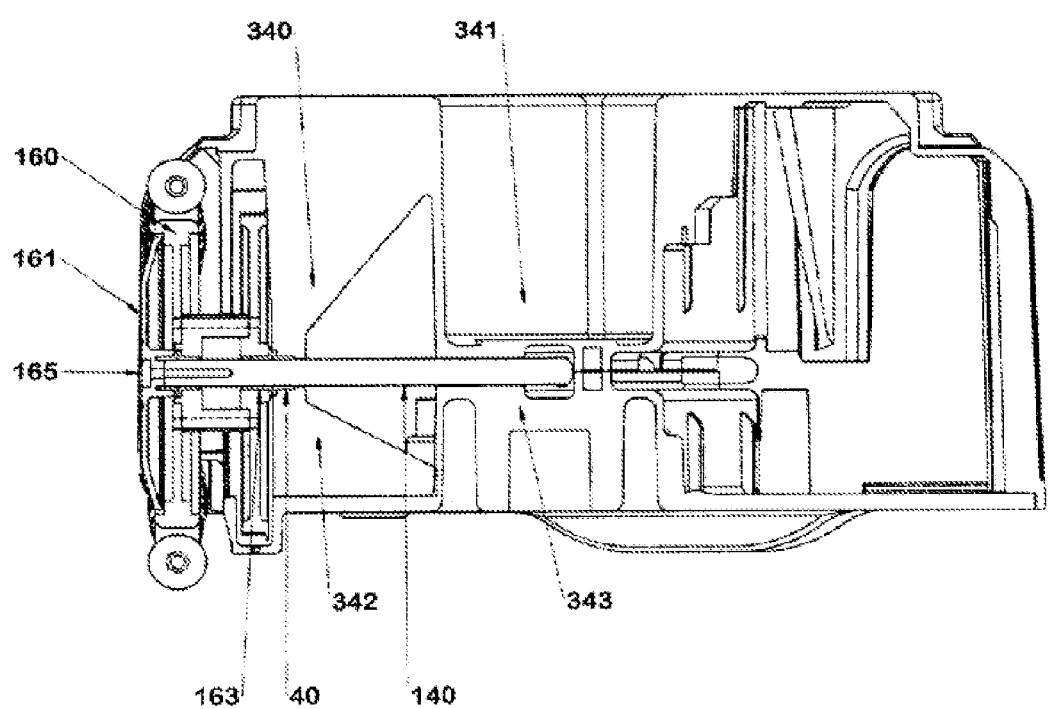
FIG. 34

MOBILE ROBOT

CROSS REFERENCE TO RELATED APPLICATIONS AND CLAIM OF PRIORITY

The present application is a continuation of U.S. application Ser. No. 16/317,353, filed Nov. 12, 2019, as a national entry of international PCT Application No. PCT/CA2017/000170, filed on Jul. 13, 2017, which claims priority to U.S. Provisional Application No. 62/361,621, filed on Jul. 13, 2016, the contents of which are all incorporated herein by reference in their entireties.

FIELD OF THE INVENTION

The present application relates to mobile robots or mobile platforms that can be customized for specific robotic applications.

BACKGROUND OF THE INVENTION

Our previous U.S. Pat. No. 8,994,776 disclosed a mobile robot that utilized a three omni-wheel design to achieve holonomic motion that included a number of distinct sub-assemblies or modules. The modular assembly provides advantages with respect to packaging and shipping with the end user completing the final assembly. This modular design also provides a mobile platform that can be customized by the end user for particular specific often specialized applications.

The ability to allow customization of the mobile robot or allowing a user to finalize or add different modules to the mobile platform is particularly advantageous in that the mobile platform can be used in multiple applications and is not limited to a solitary application.

SUMMARY OF THE INVENTION

A mobile robot according to the present invention has a base module with 3 omni-wheels, each having a separate electric drive motor connected to an electric battery supported in the base module and wherein the omni-wheels are commonly supported by a tri-axle supported in said base module.

In an aspect of the invention, the tri-axle is a single fixed component having 3 axle sections connected to each other at a central point with said axle sections extending outwardly from said central point and being located in a common plane and each omni-wheel is supported on one of said axle sections.

A mobile robot of the present invention uses a tri-axle arrangement which is cost-effective to produce, yet effectively distributes the weight of the robot, including the base module and batteries to the wheels in an efficient manner, reducing twisting or other deformations. The base module, in a preferred embodiment, includes a base shell which is preferably made by injection molding where the relatively inexpensive production part can be made of a plastic composite material with the exoskeleton design of this module significantly contributing to the final strength. This particular structure preferably cooperates with a tri-axle and allows for substantial load carrying capability of the mobile platform and also allows for modification of the mobile base module to carry higher loads by providing additional wheels on each of the ends of the tri-axle. In this design the axles do not rotate and the wheels provided on the axles rotate on stub shaft projections at each of the three ends of the tri-axle.

The present application also discloses a unique hub design where a wheel cover (or hub-cap) can be non-rotatably mounted on the axle. With this embodiment, a sensor, such as an ultrasonic or time of flight depth sensor or a computer vision camera, can be mounted in the wheel cover and the sensor can be connected with a wiring harness to a computer processor provided in the base module by a through passage in the axle if a direct connection is required. It is also possible that the sensor can be a multi-part arrangement with a portion rotating with the wheel and a nearby part or parts of such sensor arrangement held stationary and fixed to the wheel cover. Such sensor arrangement might, for example, provide a timing measurement delivering accurate wheel speed information.

In a different aspect of the invention, an arrangement is disclosed that uses two or more vertical connecting rods or long bolts that pass through the individual modules and can be tensioned to pull the modules together and thereby contribute to the structural integrity of the assembled robot. Further enhancing the structure, the lower end of these rods is preferably secured near the tri-axle in the base module shell and could also be welded perpendicularly onto the tri-axle for heavy weight applications, typically also deploying multiple wheels per end of the tri-axle. Because the end of the tri-axle does not rotate, it is also anticipated that for high load robots, additional shell or support structures could be inexpensively, and solidly, attached to each end of the tri-axle.

A further aspect of the inventive robot is a head-tilt arrangement that allows a screen, and any associated equipment that is part of the screen or touch screen, to be easily adjusted for particular applications.

In a further aspect of the invention, a motor mount arrangement is disclosed which allows different capacity motors to be used in the device depending upon the particular application. In this way the performance capabilities of the base module are easily varied, without impacting base module exoskeleton tooling.

BRIEF DESCRIPTIONS OF THE DRAWINGS

Preferred embodiments of the invention are shown in the drawings wherein:

FIG. 11 is a bottom view of the base plate according to an embodiment of the present invention;

FIGS. 12 and 13 are a side view and exploded view of the motor module according to an embodiment of the present invention;

FIG. 15 is a perspective view of the tri-axle;

FIG. 16 is an exploded view of the wheel sub-module, with the tri-axle;

FIG. 16B is a perspective view of the opposite side of the wheel hub cap in FIG. 16;

FIG. 33 is side view of the head module with the tablet in a horizontal orientation;

FIG. 34 is a section view of where the axle is within the base shell and base plate;

DETAILED DESCRIPTION OF THE INVENTION

Figure 1:
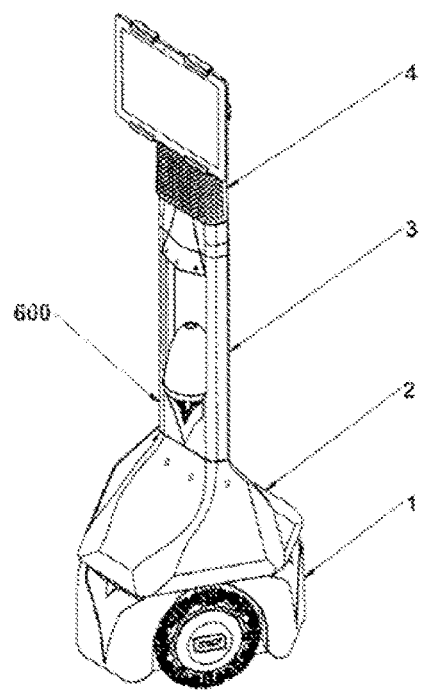
FIG. 1 is a perspective view of the virtual telepresence robot according to an embodiment of the present invention.
Figure 2:
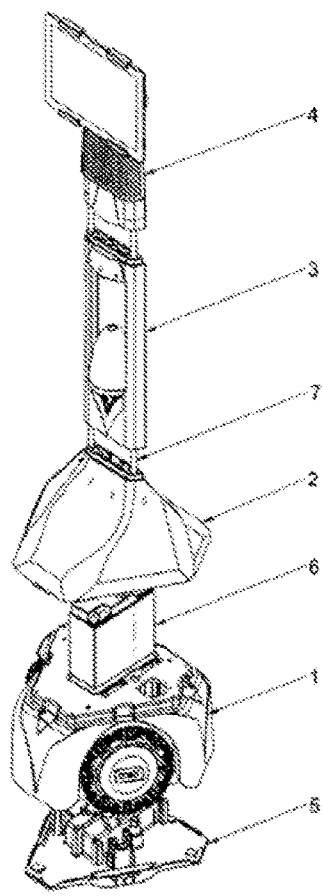
FIG. 2 is an exploded view of the virtual telepresence robot according to an embodiment of the present invention.

The mobile robot 600 as shown in FIGS. 1 to 2 has four distinct subassemblies or modules: the base sub-assembly 1, the transition sub-assembly 2, the mid-section sub-assembly 3, and the head sub-assembly 4. The base sub-assembly has a tri-axle wheel support arrangement that cooperates with the injection molded housing to improve structural integrity and load carrying capability. This relatively lightweight arrangement efficiently distributes loads to the wheels without significant deformation.

Figure 3:
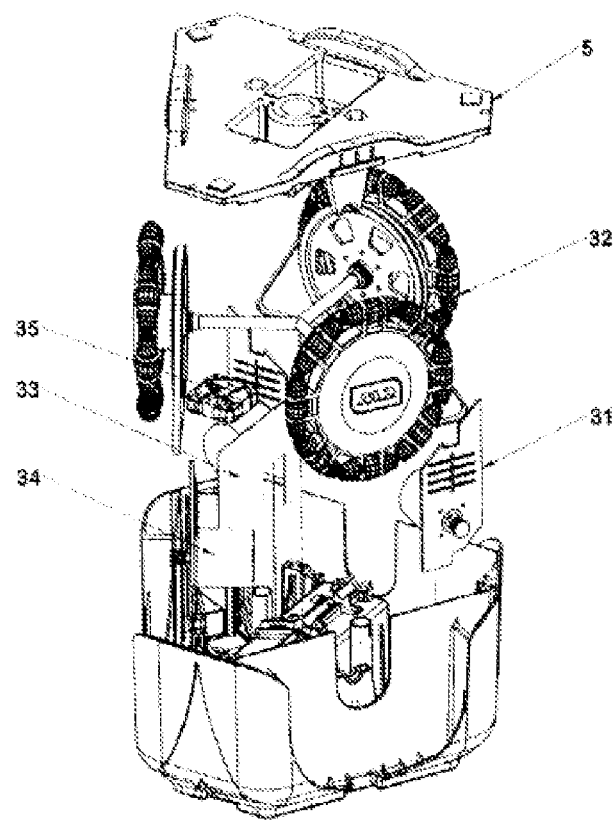
FIG. 3 is an exploded view of the base module.
Figure 4:
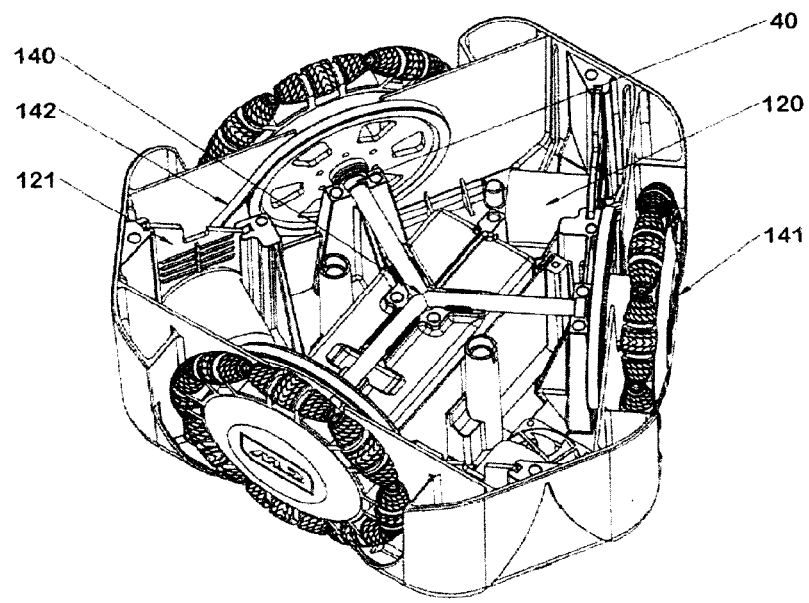
FIG. 4 is an internal perspective view of the assembled base module, minus the base plate.

Turning specifically to FIGS. 3 to 4, the base sub-assembly is now composed of several different modules: the base shell (FIGS. 5 to 8), 3 identical motor plate modules 31, the tri-axle wheel module 32, and the base plate module 5. These modules allow for improved assembly and maintainability.

The base shell is an injection molded part designed to effectively receive various components in the base sub-assembly. It is designed to be inexpensively made of injection-molded composite plastics and is both an esthetic component and, as an exoskeleton design, it also serves as a structural member. The base shell easily supports the weight of the modules above, and often the mobile robot is designed to carry significant loads as part of its customized application which often rest along the top edge 56.

Figure 5:
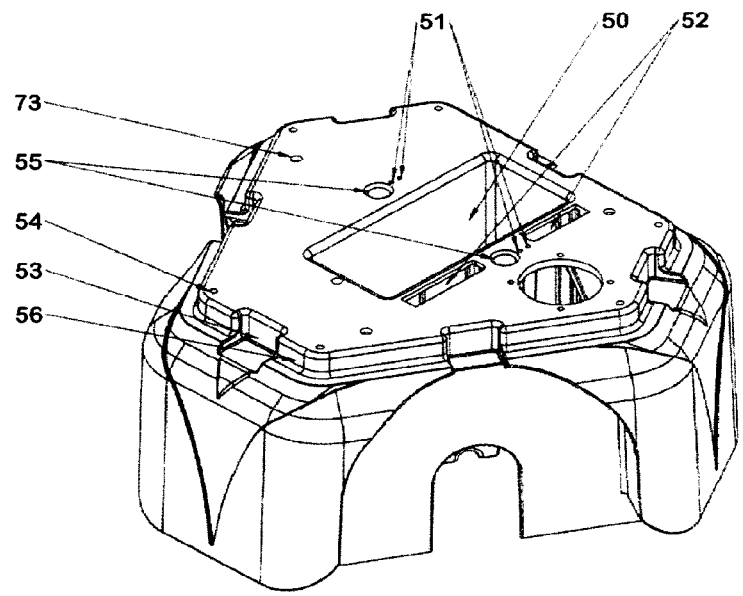
FIG. 5 is an external perspective view of the base shell according to an embodiment of the present invention.
Figure 6:
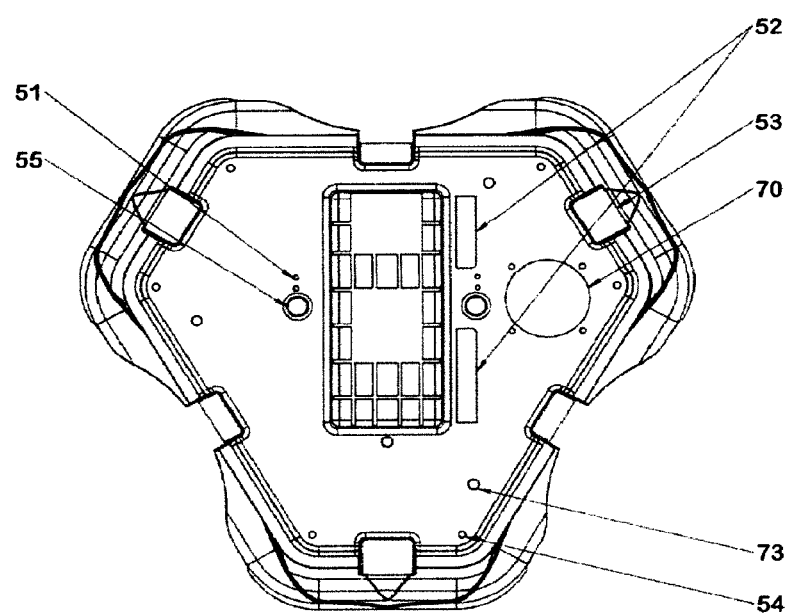
FIG. 6 is a top-down view of the base shell according to an embodiment of the present invention.

Referring to FIGS. 5 to 6, the battery compartment 50 is able to hold a standard 12V lead-acid battery. These batteries are inexpensive, widely available, and can be replaced easily. The centralized battery provides the robot with a central center of mass and a low center of gravity. The battery compartment may be lined with foam to reduce transmission of vibrations to the battery. The holes 51 may be used to affix straps in order to further secure the battery. Higher cost alternative rechargeable batteries can also be used and the compartment size can be varied to accommodate the alternate battery and maintain or improve strength and low center of gravity.

Figure 36:
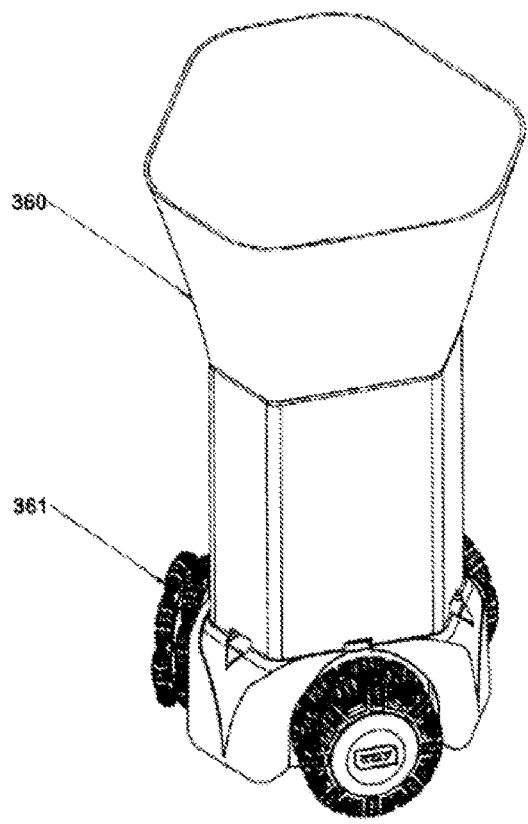
FIG. 36 is a perspective view of the shopping basket module on the base module.
Figure 37:
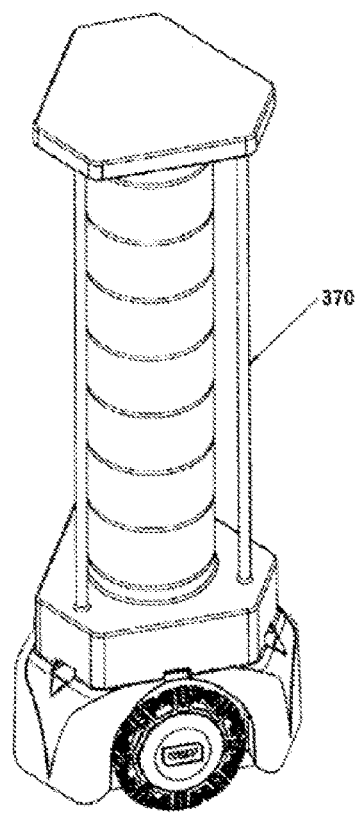
FIG. 37 is a perspective view of the vacuuming module on the base module.
Figure 38:
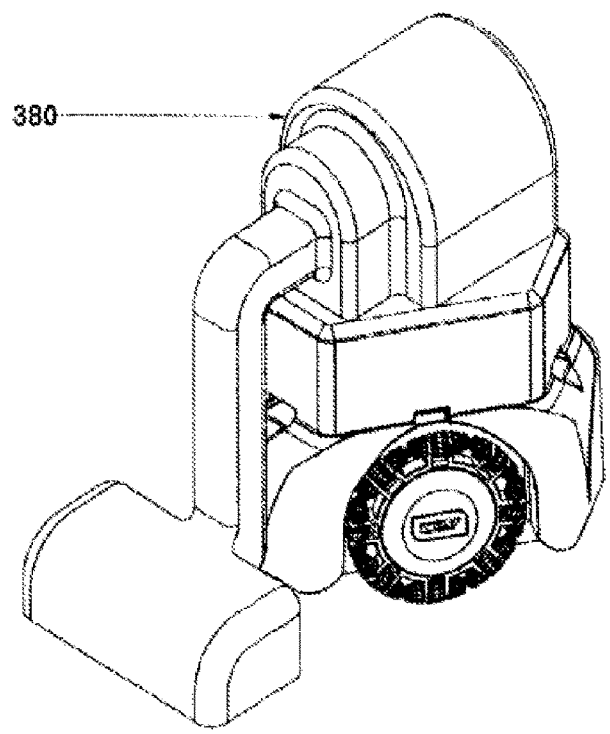
FIG. 38 is a perspective view of the ultra-violet light cleaning module on the base module.

The large slots 52 are access ports for connectors from the main circuit board 33 in FIG. 3, to connect to any circuit cards and sensors in the other upper modules. The large slots 52 provide easy access to various ports like USB and diagnostic connectors used during assembly of the robot, and debugging and programming for advanced third party users. Indentations 53 around the top edge 56 of the base shell provide support positions for various sensors including ultrasonic and infrared sensors if required. Holes 54 and the top edge 56 can be used by third parties to build customized platforms or attach other components to the base. In such a situation, the transition module or upper modules may not be needed. One such possibility is shown in FIG. 36, where a shopping basket module 360 is mounted to the base module and with appropriate software, acts as an autonomous shopping cart for a shopper or in conjunction with other autonomous picking robots. Such a shopping cart can be used in diverse applications such as order picking in warehouses to retail grocery selection are two examples. Two (2), three (3) or more wheels 361 may be mounted to each axle spoke or section to increase the robot's load carrying capacity and broaden the robot's footprint to increase stability as desired. Other customized platforms may include a vacuuming module 380 in FIG. 38 or an ultra-violet light cleaning module 370 in FIG. 37.

Figure 7:
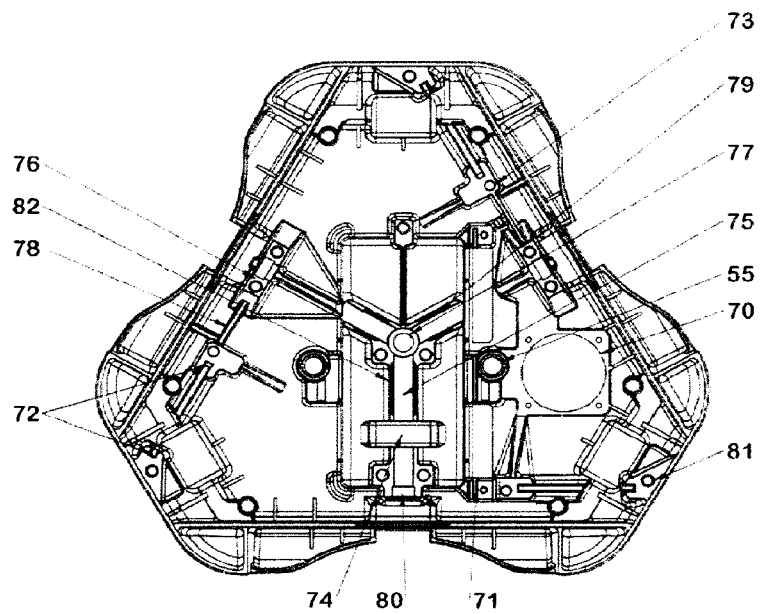
FIG. 7 is a bottom view of the base shell according to an embodiment of the present invention.
Figure 8:
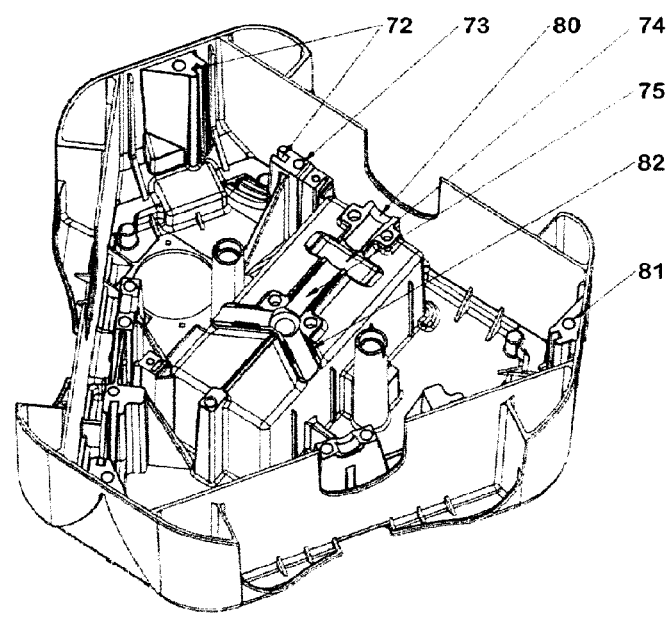
FIG. 8 is an internal perspective view of the base shell according to an embodiment of the present invention.

Referring to FIGS. 7 to 8, large hole 70 is for the fan 35, which draws air from above the base shell and pulls it into the interior of the base shell. The fan circulates the air throughout the base shell to cool the main circuit board 33 and motors 120 before exiting via the small gaps around the wheel hubs. The base shell incorporates guides 71 for the main circuit board. This is structurally inter-connected to the battery box to increase its strength. The main circuit board is intended to be one of the first parts inserted into the base module, and contains all necessary electronics components required to operate the base module separately.

The base shell also incorporates guides 72 for the motor plate sub-assemblies. These motor plate guide rails are relatively thick and cooperate with the base shell walls to improve the strength. One side of these guides is shorter than the other in order to allow the motor plate sub-assembly to be cleanly inserted into the holder after the timing belt 142 has been looped around the toothed pulley 122 on the motor shaft. They include holes 73 that go through the entirety of the base shell and can also be used by third parties to secure components as was previously discussed. Holes 81 fit screws used to secure the base plate onto the base shell, which in turn securely prevents the motor plates from moving out of their guides. There is an indentation 74 which allows passing wires from the motor on the far side of the main circuit card, without requiring longer wires on that individual motor.

The tri-axle and wheel sub-assembly 32 is held in place by 'U'-shaped channels 75. These channels meet at one end. The co-planar channels are equally spaced 120 with respect to one another to form a 360° circle. The channels have notches 82, which fit into a corresponding spot 97 on the base plate. These notches further strengthen the holder and provide protection against possible horizontal movement from any torque on the tri-axle 140. There are two axle holders 76 out apart from the main battery box holder that are also used to support the tri-axle. These are in place to provide the same amount of vertical support to these two sides as the longest axle channel, which is under the battery box. There is a large indentation 77 which can accommodate less accurate axle welds or axle weld reinforcement or coupler where the three arms or spokes of the tri-axle are joined. There are indentations 80 around the ends of the tri-axle that can be used to hold ultra-high-molecular-weight (UHMW) plastic bearings 40. There are also various walls 78 within the base plate that provide structural support as well as help channel airflow from the fan throughout the base shell.

Figure 9:
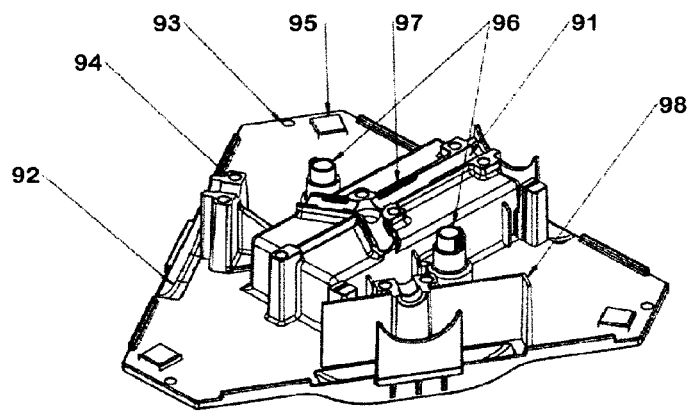
FIG. 9 is a perspective view of the base plate according to an embodiment of the present invention.
Figure 10:
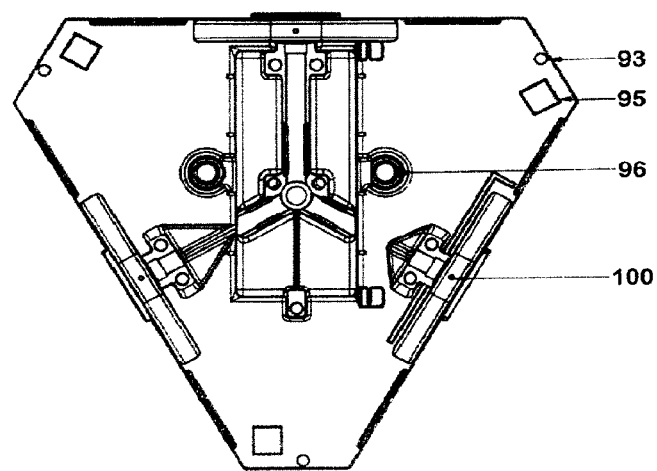
FIG. 10 is a top-down view of the base plate according to an embodiment of the present invention.

Referring to FIGS. 9 to 11, the base plate is another large injection molded component of the base sub-assembly. It has the other half of the unique tri-axle holder 91 that is part of the base shell. The base plate also increases the overall strength of the base sub-assembly. The depressions 92 in the side that provide clearance for the drive pulleys 162 of the tri-wheel axle assembly, also protrude into the base shell wall axle holes and prevent possible rotation of the base plate with the base shell, without requiring the tri-axle 140 being in place. The outer perimeter of the base plate is tightly fitted to that of the inner walls of the base shell providing further structural support and resistance to any inward bending of the base shell caused by impacts. There are multiple points of connection 93 and 94 where the base plate may be screwed onto the base shell to ensure the tri-axle is held in place securely. The design allows for the installation of sensors (like ultrasonic, time-of-flight, or infrared) 95 at each corner as well.

A further aspect of the base shell depth and base plate design concerns cases where the robot is bumped up near the head from any direction. Bumps typically push the robot up onto two wheels, with the third wheel which is closest to the source of the impact, elevating from the ground. As the robot moves up on two wheels, it then tilts until the bottom edge of the base plate between such two wheels hits the ground. This impact increases the resistance to the incoming force. Should the force overcome this further resistance, one or both of the wheels which were still on the floor now lift off the floor and the robot then begins to pivot on the edge of the base plate towards one or the other wheel which has just left the floor.

The robot is designed such that the distance from the centre point of the base plate between any two wheels and the ground at this point will be closed to zero in the event of a bump before the robot's centre of gravity is beyond the touch points on the ground. Thus, the robot will self-right if the force is removed before the two wheels have left the floor.

Furthermore, the robot is designed such that if the force continues, and these two wheels leave the floor and the robot pivots on the base plate between such two elevated wheels toward one wheel, in many cases, the robot will still right itself since the centre of gravity is still behind the point or points of contact with the ground.

Holders 96 are for the vertical connecting rods or long bolts 7, which are screwed into the press fit hex nuts 111 on the underside of the base plate. Walls 98 are to direct airflow from the fan to not exit the base plate from specific sides but to instead flow around to the opposite side of the base an out around the axle for the far wheel. Those walls may also provide additional protection from water and debris entering along the axle sections. Small holes 100 allow any water or other liquid that may have entered past the wheel module 141 and onto the base plate, to drain back to the external environment. The base plate may also include a central charging apparatus (such as an induction charging pad) 110 that allows for recharging the battery no matter what direction the robot may be facing.

Referring to FIGS. 12 to 13, the motor plate subassembly is designed to be easily slid into grooves or tracks in the base shell and thus these components can be easily maintained or replaced. The preferred embodiment utilizes a DC brushless motor 120 mounted to a motor mounting plate 121 such that the toothed pulley 122 on the motor shaft extends through the mounting plate. The toothed pulley on the motor shaft is then situated in a coplanar manner with the large toothed drive pulley 162 on the tri-axle wheel assembly 32. Although these pulleys feature flanges on one or both sides of the teeth, if flex between the motor and drive pulley was such that these two pulleys would no longer be coplanar, the belt 142 would have an increased likelihood of derailing. The tri-axle integrity in cooperation with the base shell provides a number of advantages.

Figure 13B:
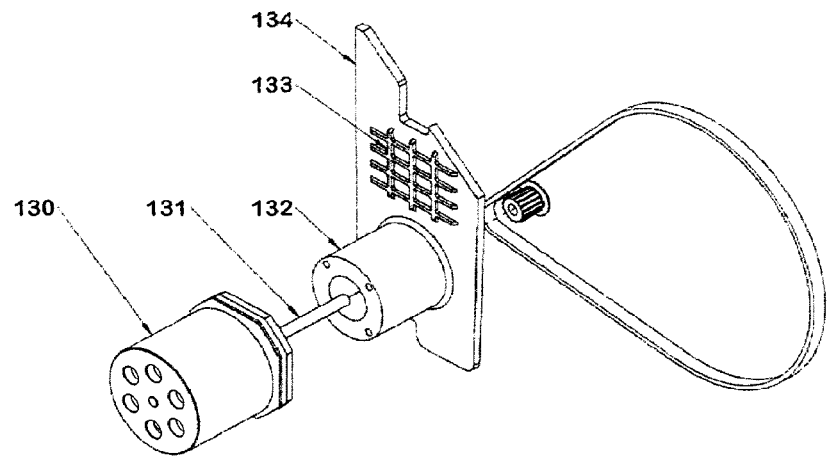
FIG. 13B is another possible embodiment of the motor module.

The position of the motor on the motor plate as well as the diameter of toothed drive pulley can be adjusted to achieve different gear-reduction ratios as required. Ribbing 123 provides some structural support to the motor plate to protect against resonance, and also acts as a grip for the user. Motor seat 124 allows for accommodating different motors with varying shaft lengths, and may be a separate component from the motor plate. Screws 125 secure the motor 120 to the motor plate 121. The positions of those screws can be moved and is not in the path of the timing belt 142. FIG. 13B shows a different embodiment of the motor plate module. In this embodiment, the motor 130 has a longer shaft 131, and as such the motor plate 134 has a similarly longer motor seat 132 to accommodate the longer shaft. The ribbing 133 is different to account for the different resonant characteristics of this motor. This embodiment also illustrates that out runner-type motors (like 130) can be used with freely rotating components with respect to the motor plate, rather than just fixed case motors (like 120). There is sufficient room in the vicinity of where the motor modules are placed within the base shell to accommodate various wiring arrangements, motor sizes, and motor shaft lengths without the need for retooling of the base shell.

Figure 14:
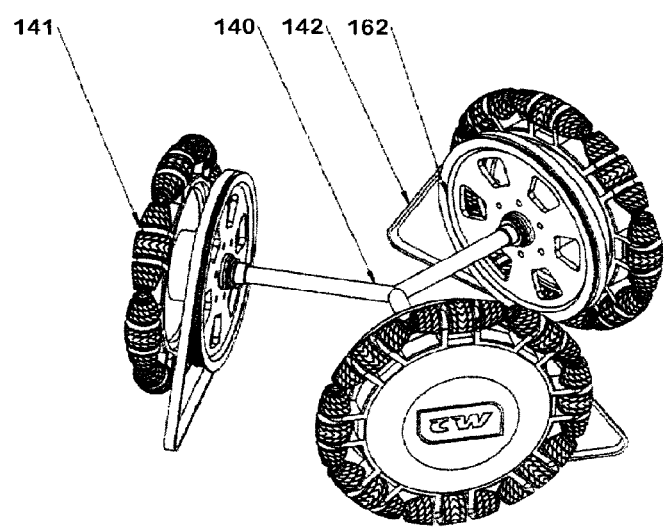
FIG. 14 is a perspective view of the assembled wheel tri-axle module.

Referring to FIGS. 14 to 15, the tri-axle wheel assembly consists of a tri-axle 140 and three identical wheel sub-assemblies 141. The tri-axle in the preferred embodiment has three cylindrical rods or spokes 150 positioned on a plane surface at 120 with respect to one another, making a 360° circle, and welded at the point where the these three rods intersect 151. The weld must be sufficiently strong to ensure the axles are essentially one piece, and do not move with respect to one another. There are slots 152 and holes 153 at the end of each axle that fit into a corresponding area (168 in FIG. 16B), to keep the wheel hub cap from rotating with respect to the tri-axle when affixed with screw 165.

Now referring to FIG. 16, the wheel sub-assembly consists of the omni-wheel sub-assembly 160, wheel hub cap 161, three plastic bearings 163, and the toothed drive pulley 162. The UHMW plastic bearings are pressed into the hole on the drive pulley, the omni-wheel hub, and the wheel hub cap (visible in FIG. 16B). These plastic bearings have a low coefficient of friction and allow the wheel sub-assemblies to rotate freely with respect to the tri-axle, while being constrained between the wheel hub cap 161 and the axle holder on the base shell 76. In the present embodiment, these bearings will not require any lubrication, which can be hazardous in the cases of leaks in some service environments, like medical facilities. These bearings can also include slotted polymer bushing designs enabling the robot to operate in sandy conditions where the slots effectively clear sand and dirt from the axle segments. Screw 165 goes through the wheel module and screws into the hole 153 at the end of the tri-axle. Cap cover 164 can be used to hide the screw to improve aesthetics of the hub cap.

Figure 17:
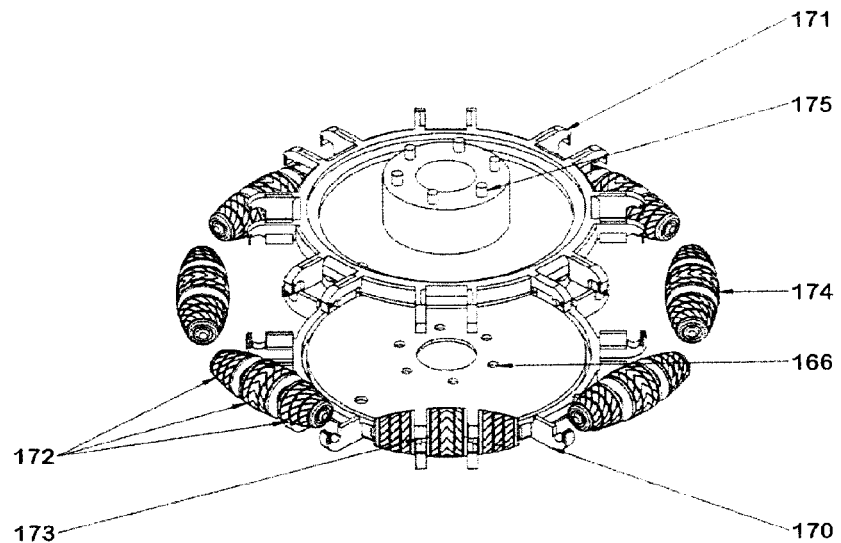
FIG. 17 is an exploded view of the wheel hub subassembly.

The omni-wheel sub-assembly is seen in FIG. 17. The omni-wheel is split into two halves 170 and 171. These allow for easy assembly and replacement of the rollers 172 or roller axles 173. One half 170 of the omni-wheel remains stationary, while the roller assemblies 174 are placed into it. The other half 171 is then pressed onto the stationary half 170, securing the roller assemblies in place. A timing belt 142 is looped around the drive pulley before the wheel sub-assembly is secured onto the tri-axle. Protrusions 175 fit into holes 167 of the drive pulley 162 to ensure that when the pulley is turned by the motor, the omni-wheel turns.

Figure 18:
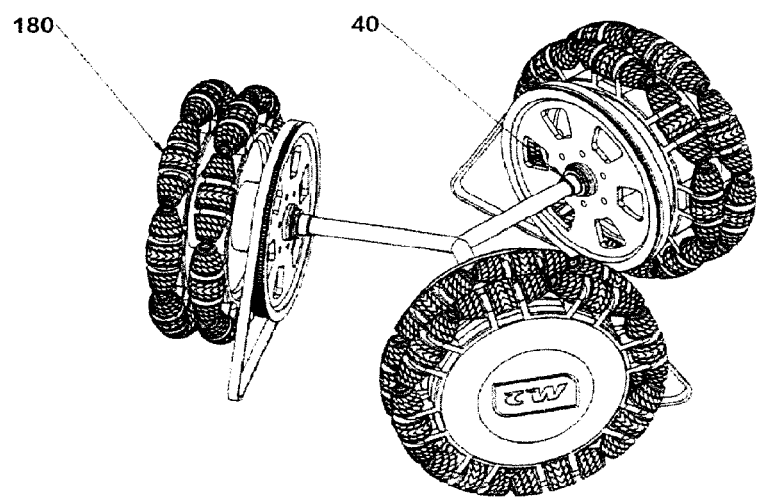
FIG. 18 is a perspective view of double wheels on the tri-axle.

It is also possible to add a second omni-wheel 180 onto the axle shown in FIG. 18, allowing for two omni-wheels per axle, and a greater carrying capacity for the base. Even more wheels could be placed onto the axle in a similar manner to further increase stability, carrying capacity and broaden the footprint of the robot, like 361 in FIG. 36, although a longer axle may be required in some cases. The second omni-wheel hub's protrusions 175 would fit into holes 166 of the first wheel hub. Those holes and protrusions are slightly offset from one another, so that any additional omni-wheel hub's rollers will have a different orientation from the previous one. This also allows for greater roller to ground contact at the angles where there was previously minimal contact with a single omni-wheel (such as the area between two roller assemblies). The omni-wheel hub cap 161 is screwed onto the end of the tri-axle. Having stationary wheel hub caps allows company or client branding to remain upright at all times during the robot's motion.

Figure 19:
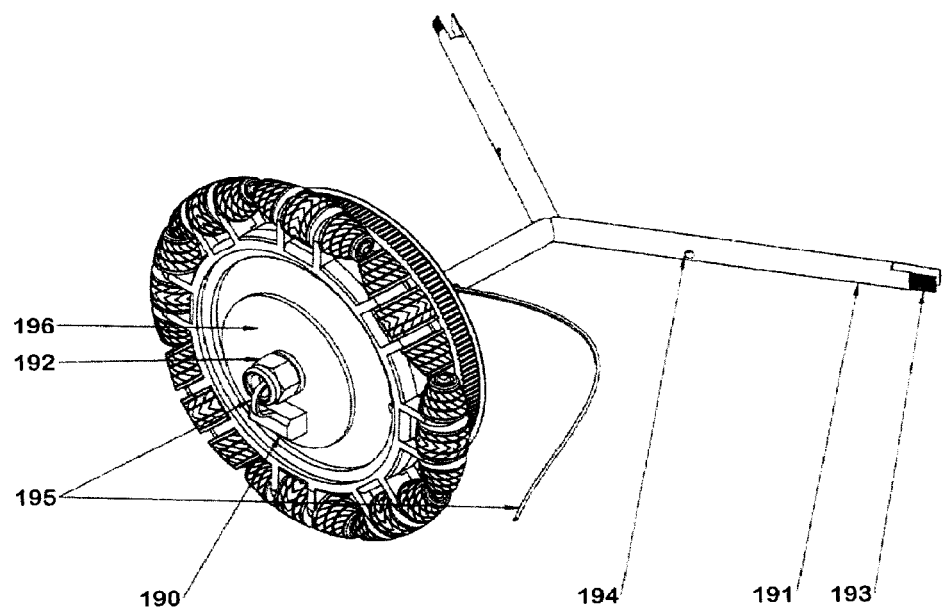
FIG. 19 is a perspective view of the wheel hub cap with the sensor.

Hub motors to power the omni-wheels instead of the belt drive arrangement, and infrared, time-of-flight, or ultrasonic sensors 190 may be affixed to the tri-axle segments. Sensors are typically placed on the hub cap, as seen in FIG. 19. In such a case, a longer hollowed out tri-axle 191 could be used to accommodate the wiring 195 from such sensors (or hub motors). Wiring may be thin ribbon cable to allow the wire to exit holes 194 and plug into a connector on the main circuit card 33. Holes 194 may have some insulator to hold the wire in place and at a fixed length. To wire the sensor through the axle to the main circuit board 33, the screw 165 cannot be used like FIG. 16. To secure this wheel hub cap 196, the end of the tri-axle segment 191 would instead be threaded 193 and held by a nut 195. This embodiment shows a different small wheel hub cap 196, and does not show the larger wheel hub cap that would typically encase the end of the nut 195 and protect the components in front of 196, while leaving room for sensor 190 to see the ground.

Figure 20:
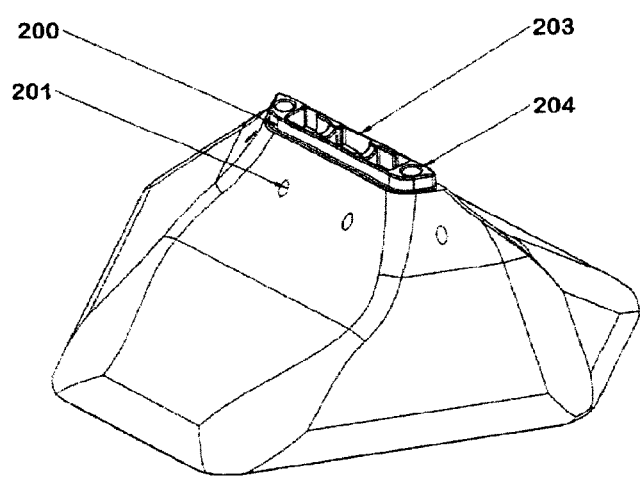
FIG. 20 is an external perspective view of the transition module.
Figures 21, 22:
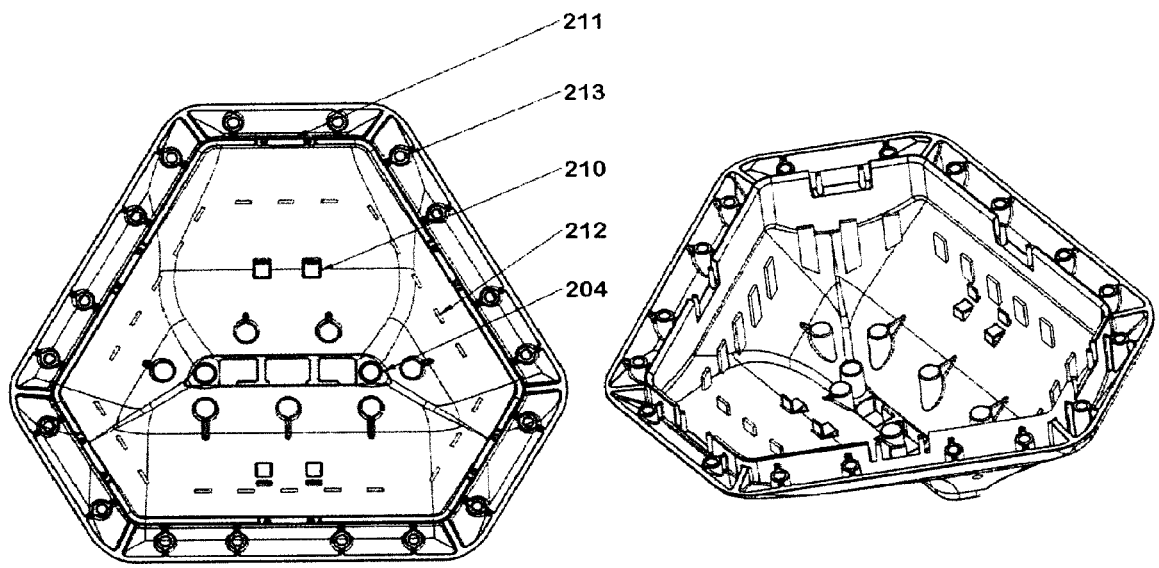
FIG. 21 is a bottom view of the transition module.
FIG. 22 is an internal perspective view of the transition module.
Figures 23, 24:
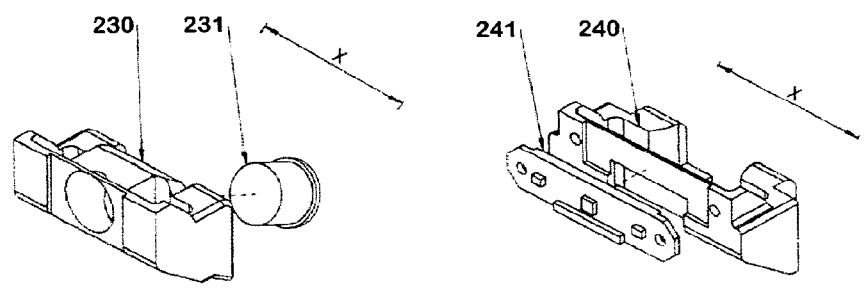
FIGS. 23 and 24 are exploded views of possible sensors and sensors mounts for the transition module.
Figure 25:
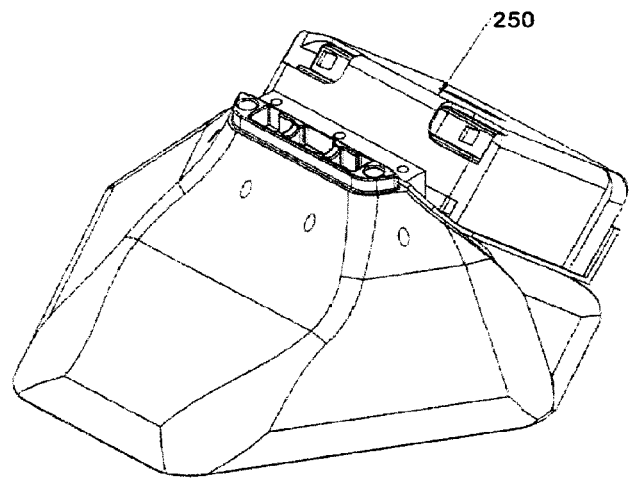
FIG. 25 is a perspective view of the extra battery compartment.
Figure 26:
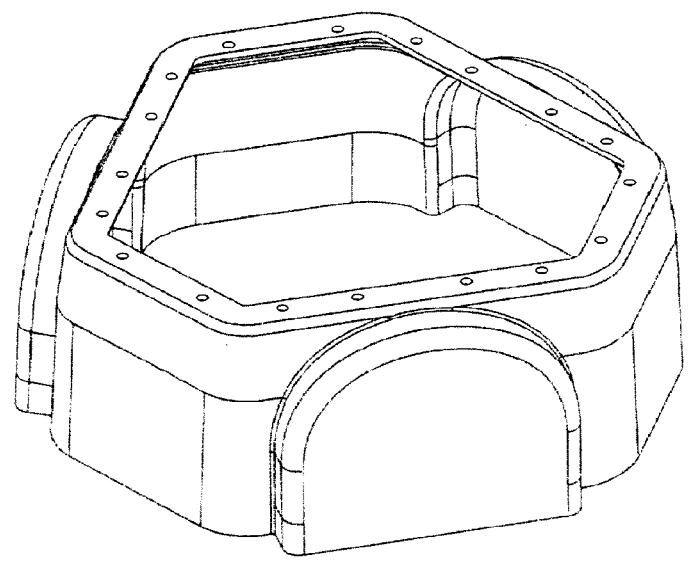
FIG. 26 is a perspective view of the rain cover module for a double-wheeled base.
Figure 27:
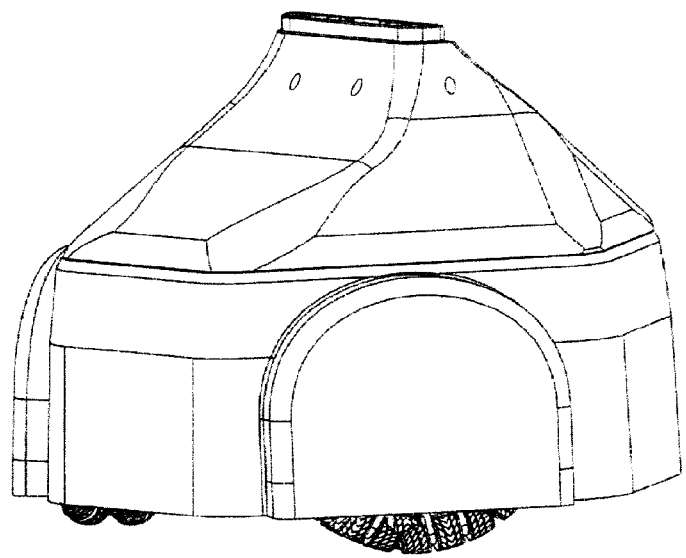
FIG. 27 is the rain module cover in FIG. 26 on a doubled-wheeled base.
Figure 28:
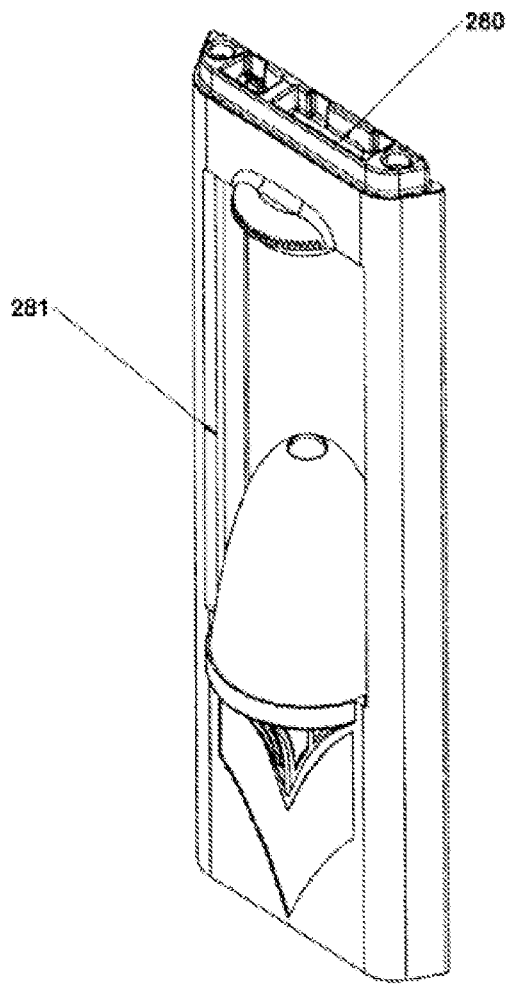
FIG. 28 is a perspective view of the mid-section module.

The transition section module is shown in FIGS. 20 to 22. The transition section is a relatively large injection molded part, but has a similar height as the base shell to ensure easier packaging and shipping to the consumer. The transition section has the same triangular base profile as the base shell, but then tapers off higher up to create a rectangular/trapezoidal shape 200 that provides the guiding shape for the midsection (FIG. 28). The transition fits tightly around the lip of the base shell, to provide strength and minimize any vibrational noise during the robot's movement. There are small guides 210 that help keep the battery locked into place. The transition incorporates slots 211, with a spacing of X, around its six edges that allow for placement for sensor modules seen in FIGS. 22 to 23. These sensor modules can be in a variety of shapes and sizes (as long as their rear dimension does not exceed X), and can be created by third parties as well. These modules can hold various sensors, including ultrasonic and infrared. These sensors may be used to detect an object's proximity to the base and prevent collision with the object. Another example is being able to detect the edge of downward stairs, and prevent the robot from falling down them. There are also wire clips 212 around the periphery that can keep the wires from the sensor modules organized. At the top of the transition section there are various holes 203 and 204. These holes 203 allow air to be pulled down through the transition section from the mid-section sub-assembly, in order to reach the fan 35 on the base sub-assembly. These holes 203 also allow wires from connectors on the main circuit board 33 of the base sub-assembly to pass through the transition section, so that they can connect with the circuit boards in the mid-section module. Holes 204 allow for pass-through of long bolts 7. There are several indentations 201 that allow for connection of various first or third party peripherals. One such use is for a guide for the holder for a second battery FIG. 25, which doubles the runtime of the robot. Holes 213 are also used for attachment of a rain cover accessory as seen in FIGS. 26 and 27. This rain cover accessory is intended for waterproofing an outdoor version of the robot. This module would preferably be secured to each section of the tri-axle at their outer ends using screws threaded into holes 153, and may not require the wheel hub cap 161.

Figure 29:
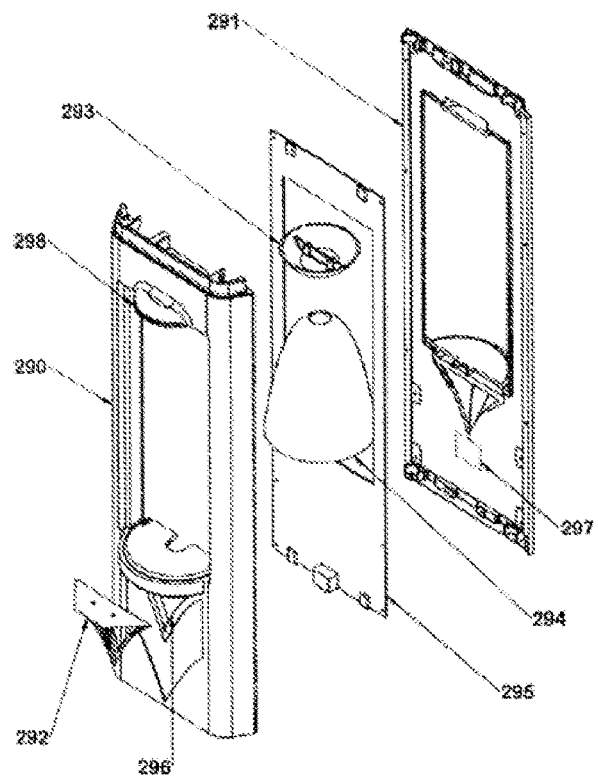
FIG. 29 is an exploded view of the mid-section module.
Figure 30:
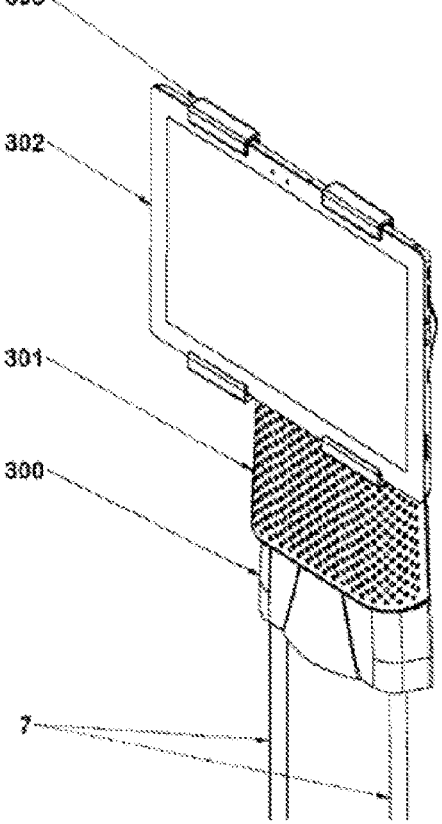
FIG. 30 is a perspective view of the head module.
Figure 31:
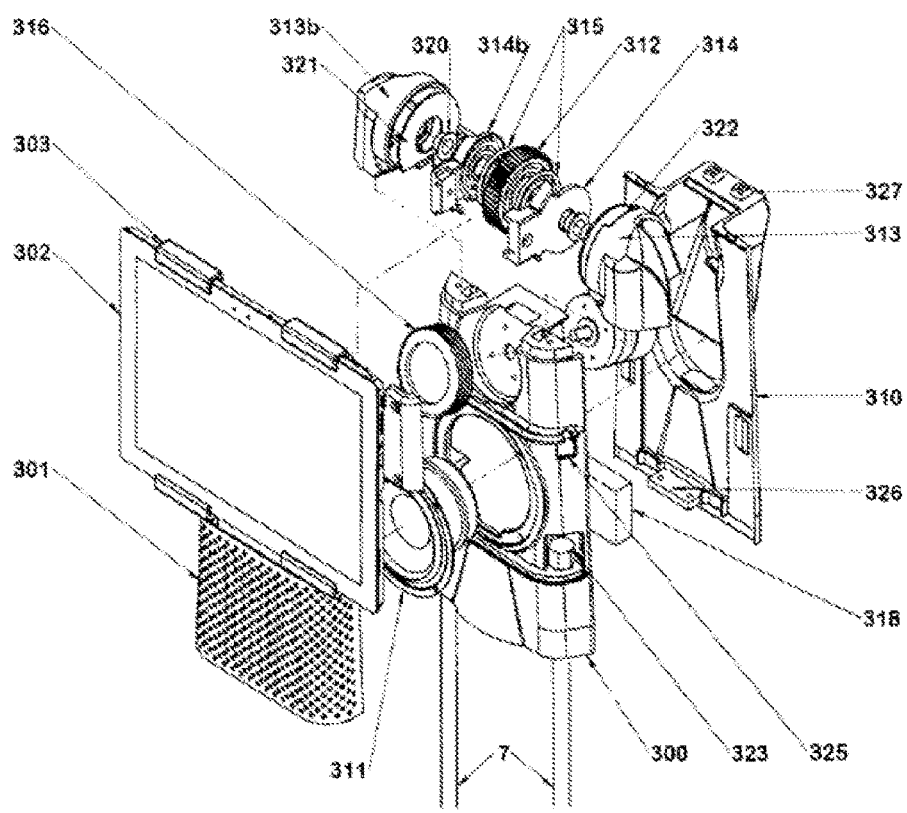
FIG. 31 is an exploded perspective view of the head module.
Figure 32:
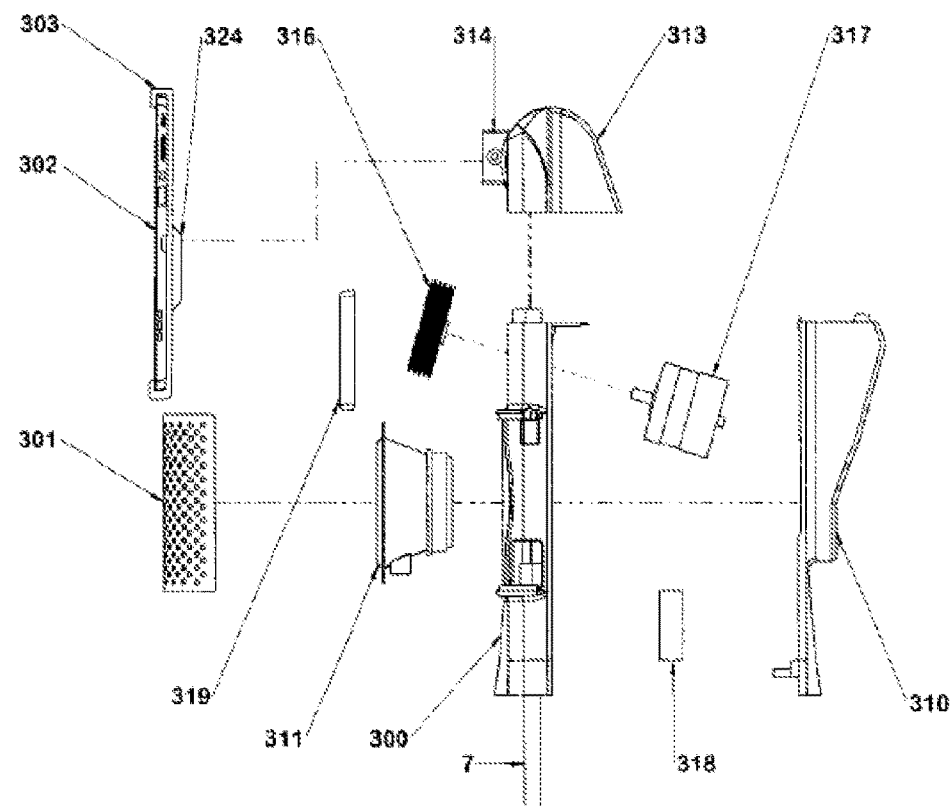
FIG. 32 is an exploded side view of the head module.

The mid-section module is shown in FIGS. 28 to 29. The mid-section module includes the front half 290, the back half 291, fan grill 292, two reflective domes 293 and 294, and the mid-section circuit board 295. The mid-section has two main injection molded parts; the front half and the back half The front half has a hole 296 that allows air to flow from the mid-section downwards into the transition section, so that the fan 35 in the base shell sub-assembly can pull the air into the base shell to cool the main circuit board 33 and the mid-section circuit board. The hole 296 is covered by a fan grill 292, which can prevent dust and debris from entering the robot with a removable mesh lining. 298 indicates an area that may be used as a microphone or as another speaker. 292, 293 and 294 may be mountable to 290 and 291 through the use of magnets to allow for easy maintenance or replacement. The indentation 280 is an area that can hold wire from one of the USB type-c connectors, since there is little room between the top of the mid-section circuit board and the circuit board in the head module. The mid-section circuit board is screwed securely onto the back half, and it acts as the host for the robot. A shutdown button 297 may be included on the back half, to provide an easily accessible area for the user to manually power down the robot. The two reflective domes are used for the vision system. As was mentioned in the US Patent 8,994,776, there are obstructions in the view at 90° and 270 due to the design of the midsection, however these blind spots in the vision have been reduced due to the reduced curved profile around those areas 281.

The head module is shown in FIGS. 30 to 33. In the present embodiment, the head module includes the tablet 302, tablet mount 303, front half 300, back half 310, top holders 313 and 313b, speaker 311, speaker grill 301, head circuit board 318, motor 317, worm 316, worm gear 312, worm protector 319, worm gear covers 314 and 314b, O-rings 315, top holder spacers 321, and several plastic bearings 320. The tablet is mounted at such a height so that the user can maintain comfortable eye contact with others. The tablet mounts are interchangeable to allow the user to use whatever tablet they prefer or currently own. A third party may also choose to use a modified tablet mount 303 to mount other small sensors to augment the robot capabilities, such as an Intel RealSense® sensor.

Although the head is mounted at a fixed height in this embodiment (which could easily be changed with a longer or shorter head module, or a spacer between such modules), it can still tilt within a large range of approximately 340. With this design supporting a large range of motion, when desired, the tablet can almost completely flip to a rear-facing position, as shown in FIG. 33. In such a position, for example, a user can view and use the tablet screen while the robot can move forwards with the optimal orientation of the omni-wheels with regards to speed and stability. An example of such a case could be an elderly person using the robot as a walker (with another customized module). The tablet is able to quickly and quietly tilt through the use of the brushless dc motor 317, which might also be the same ones used in the base to achieve further volume cost reductions. The speed of this motor enables the tablet to "nod" quickly up and down, under software control, should the robot be operating in an autonomous mode and wish to acknowledge a command or other visual or auditable signal. A further advantage of the reverse tablet position is in cases where the tablet has internal "depth" and structure mapping capabilities (typical of Google "Tango®" and other augmented reality systems) and needs to verify a path in a forward or reverse direction or to enable avatar-like capabilities where a remote telepresence user is able to see and experience the world through the robot. In all such cases, the bracket adapter holding such third-party tablets or cell phones or other devices must ensure that embedded cameras are not obscured by such bracket.

A further advantage of the speed of tilt can be understood by looking at the example of a restaurant or theme park operator. When deploying these robots in autonomous operations to take food orders or assist in crowd and queue management, the robot may be bumped in such a manner that it would topple over. During the fall, gyros in the system will anticipate the point of impact and quickly tilt the tablet or integrated display to a position where it will not hit the ground. Typically, taller telepresence and other larger robots are not able to re-configure themselves during a fall and suffer serious damage. The modular robot design anticipates a fall and through reinforcement of the speaker housing and on the reverse side, the motor housing, a fall will not result in structural damage, and assuming the display is autonomously tilted out of the way, the display will not be damaged either.

Compared to U.S. Pat. No. 8,994,776, the improved design has the motor on the back of the head module, thus making it more hidden and aesthetically pleasing. There are also array microphones and a large speaker 311 incorporated into the design, which allows the user to more effectively communicate with others (especially in noisy environments or with hearing impaired people), versus just the tablet's speakers and microphones.

Although the figures illustrate a separate tablet mounted to the head tilt assembly, some robots using this system can include integrated displays which mount directly in the bracket and cannot be removed by an end-user.

The speaker grill 301 is designed in such a way to not protrude too far from the front half 300, and it flows into the sides of 300 rather than wrapping around onto the back half 310, to increase aesthetic appeal and provide easier maintenance. The speaker grill and following worm protector may also be attachable with magnets, similar to 292, 293, and 294 in the midsection module. The worm protector 319 protects the user from the worm and worm gear teeth from the front. It provides a suitable surface stop for the tablet mount 303 as well. Also, on the top of 313 and 313b a flexible rubber or bristle-like material that protects the user from the teeth of 312 from the rear. Worm gear covers 314 and 314b straddle both sides of the worm gear 312, and their shape allows them to move freely through the aforementioned material. 314 and 314b have holes that allow for secure mounting to 303 at area 324. O-rings 315 are placed between 312 and 314/314b. The purpose of the O-rings 315 is to allow the tablet to be manually moved to any position (such as a doctor or nurse moving it into a writing position) without causing any damage to gears 312 or 316. The channels in 312, 314 and 314b have ridges which provide a sufficient amount of friction for 315 such that the tablet will not droop due to gravity, but the tablet can be moved with sufficient manual force. Spacers 321 may be used to adjust the amount of force on 315. Areas 322 and 325 are to allow for pass-through of wires from within the head module to the tablet 302. Area 323 provides a space to tighten the long bolts 7 that will be further discussed later. Areas 323 and 325 are hidden from view once the speaker grill is placed on the front half. Nuts in 323 must be loosened in order to disassemble the head module 4. There are no exterior facing screws (to increase aesthetic appeal) to completely disassemble 4. Rather screws at 326 and tabs at 327 keep 4 together, and are held down by 313 and 313b. There is an axle embedded into 313 which provides the central axis for head tilt.

The design allows for force sensors to be installed within the head tilt assembly where the bracket joins to the assembly so that a powered response to external, manually applied tilting forces (like those applied by a user simply trying to re-adjust the tilt) may be used to ease such tilting by driving the motor in a direction corresponding to the manually applied force. In the case of a senior or physically challenged user for example, a light touch could then be applied to re-position the head rather than pulling it manually against the friction of the O-rings. These force sensors could also be used to detect possible pinched fingers or other end limits of motion by software algorithms which would correspondingly limit or modify motor speed and direction in response to such external forces.

The lips 56 and 200 that the base shell and transition sections have are also a part of the midsection and head modules. The areas where the lips enter the module directly above them are hollowed out to match the size of the lip and provide a tight fit between modules. With the lip connectors being a direct part of each main module of the robot, extra connectors like screws are not required between adjacent main modules. This allows for allow for quick and easy assembly without fastening by an unskilled consumer. Similarly, this allows for quick and easy disassembly or replacement of modules, without requiring extra tools. The protruding lip connectors are placed on the top of the modules rather than the bottom, which provides protection to the electronics in the event of rain or water around those areas. If the top of the modules was a hollowed out section rather than a protruding lip, water could potentially drip in due to gravity and damage various electronic components.

Although the lips provide a tight connection between main modules, there may still be a possibility of an upper module becoming detached from the base module and transition section due to application of a strong vertical or horizontal force. Therefore, long bolts 7 (FIG. 2) are placed vertically inside of the robot. They extend through the head module and go through every main module ending at the base plate where they are tightened into the press fit nuts. The long bolts may be split into two parts to allow for easier shipping and overall assembly by user. These bolts provide a strong compressive backbone for the robot increasing its overall structural strength, and prevent the main modules from becoming unintentionally detached from one another.

Figure 35:
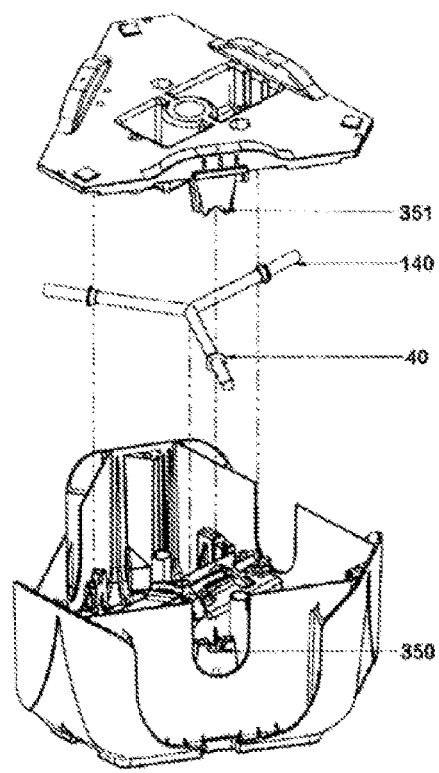
FIG. 35 is an exploded view of the tri-axle's placement within the base shell and base plate.

FIGS. 34 and 35 illustrate the tri-axle supported within the base module. FIG. 34 shows a cross-section of the tri-axle support within the base module. Tri-axle 140 is held in place by 340 and 341 from the base shell, and 342 and 343 from the base plate. 340 and 342 are separate axle supports spaced away from the central weld of the tri-axle 151 in FIG. 15, the same distance as the support on the battery box labelled as 80 in FIG. 7. This equal spacing provides an equal distribution of forces on the tri-axle. 341 and 343 just indicate areas around the axle channels on the battery box that support the axle as well. FIG. 35 shows a view of the tri-axle with some bearings and where their respective place is within the axle supports. For example, the individual bearing labelled as 40 fits within 350 of the base shell and 351 of the base plate.

As shown in the drawings, the tri-axle arrangement is a one piece solid axle or a three piece axle having a very strong central connection that is supported outwardly at the wheels and is not prone to deflection. This axle can be of different lengths if additional wheels are required or the wheels can actually be coupled to themselves with only a single wheel connected to the axle. The axle can be made to carry high loads and effectively the weight on the base module is transferred from the wheels to the axle via the various wheel bearings or bushings in the base module and the number of transfer locations can be adjusted to more effectively distribute the forces through the base module and support different upper module configurations.

This disclosed tri-axle design is effective in distributing forces while also significantly reducing distortions of the overall base module of the robot, not only due to loading from upper module payloads, but also due to unexpected impact or collision. It also enables one or more omni-wheels at each of the ends of the sections or spokes of the tri-axle to rotate and be powered by the motors as shown in the drawings. The drawings clearly show the use of multiple wheels for each axle which can be of great assistance in effectively reducing the load per omni-wheel allowing a lower cost wheel to be used and to enable a wheel that is designed for lighter applications to be deployed in a double or triple or larger combination for carrying higher loads or operating on softer surfaces. The omni-wheel design continues to function in the normal manner whether used individually or used in combination with other omni-wheels. The base module has also been divided essentially horizontally to allow the tri-axle to be placed in the base unit with the bearing support portions being part of the base molding. Additional components can then be added and a bottom plate 5 is also used to provide a further structural component and mount for circuitry 33 etc. As shown in FIG. 3 (where the base module is inverted for illustration purposes), the motor drives 34 for the individual or sets of wheels 32 at the ends of the tri-axle are mounted on separate slider-card mounts 31 for stiffening of the injection molding base module as well as allowing the motor drive arrangement to be inserted as a finished unit as it simplifies the assembly of the base unit and also allows the base unit to be easily customized for different applications and power requirements. Each of the individual motors preferably include their own fan unit 35 for cooling or selective cooling as required. It is possible to re-use a single fan within the lower chamber of the base unit for drawing of air into the base unit and out thereof for cooling the components. In this way the mount board of the motors cooperates with the base module to increase strength.

Preferably the individual modules of the mobile robot are interconnected by two or more vertical rods 7 as illustrated in FIG. 2 that pass through bearing type portions of each of the modules. These rods provide a common vertical support reinforcing the connection of the modules and the rods preferably include an arrangement for applying a compressive force to the individual modules to draw them together with respect to the vertical direction. With this arrangement, the rods significantly increase the structural integrity of the connected modules and integrate the modular components in a cost effective manner. In the present design, two rods as shown are particularly desirable as the center portion of one of the modules includes a large port to allow effective viewing both forwardly and rearwardly and as much as possible to each of the sides. Viewing in the vertical planes is also advantageously provided by the two opposed domes. The use of two rods either side of this large center opening has proven effective. The rods are preferably of a metal or a high strength reinforced plastic material. Although in the figures, these rods enter and are secured in the base module at either side of the battery compartment within the plastic composite exoskeleton, where maximal strength is required, rods can be perpendicularly welded to the tri-axle itself. Alternatively, one of more nut or other connectors can be welded or affixed onto the upper surface of the tri-axle, or the tri-axle could have a bored threaded hole, such that the vertical rods can thread or otherwise be attached to the tri-axle at any point. Support structures or rods need not be attached to the tri-axle inside of the wheels. For example, each axle arm or spoke of the tri-axle can extend beyond the wheel or set of wheels and at its extremely, a bored and threaded hole can then be made available for perpendicular rod attachment. Alternatively, threads at the end of each axle arm or spoke of the tri-axle can accept mating structural components.

FIGS. 15 and 16 clearly illustrate how an individual omni-wheel is rotatably supported on the stationary axle arm 140 of the tri-axle by means of bearings 163. The drive pully 162 is mechanically secured to the omni-wheel and includes a toothed surface for cooperating with the notched drive belt. The wheel hub 163 can be mechanically fastened by the bolt 165 to the axle arm 140. This wheel cover 161 can engage the slot 152 provided at the end of the axle arm such that the wheel cover does not rotate. This fixed, non-rotating cover offers a number of aesthetic visual design choices, but more importantly, with this arrangement, the wheel cover can provide a support position for the sensor or part of the sensor used to sense a wheel movement. Any electric connection can also passed through the axle if desired. In addition to sensing wheel movement, other sensors can be provided in the wheel cover 161 and the position of the sensors can be known as the wheel cover need not rotate. Such an arrangement is shown in FIG. 19.

A further advantage of the fixed, non-rotating wheel cover is an optional employment of hub motors instead of the toothed belt drive or possible gear drive. Because the wheel cover doesn't rotate, the tri-axle design could use the channel inside the axle to carry power and control signal wires feeding one or more hub motors. The powered coils for these motors would be stationary on each arm or spoke of the tri-axle while permeant magnets or, in the case of axial-flux type motors, coils, would be mounted within the spinning part of one or more wheels on each of such axle arms.

Returning to the base module and structure as shown in FIG. 3, the motor mount arrangement 31 allows for different size of motors to be available and for the mobile robot to be easily customized for a particular user's requirement without modifying costly tooling for the base module exoskeleton shell. It has been found that while robots with mobile platforms have many diverse applications, these applications commonly require a base unit having the necessary wheels and axle support etc. as well as power drives for moving of the base unit about its environment. There is a large market for such a mobile base where disparate users can effectively use the mobile base as a component of their customized process or application. In the present application, the base unit, drive for the base unit, as well as power that is available at the base unit for driving other user determined requirements is advantageously used by individuals in companies seeking to offer their own customized mobile platform. This particular base unit with its ability to easily change a power drive arrangement for the wheels, the ability to provide additional wheels for higher load carrying capabilities and a larger, more stable footprint, the ability to use different sensors generating a variety of sources of information, in combination with providing a base where a user can easily provide instructions to the power base in an appropriate manner and in any direction, is very advantageous.

The Applicant has found the welded tri-axle arrangement particularly for higher load applications can be made of high strength steel and the base unit can be designed for distributing the force on the axles throughout the base module. It can be appreciated that the base unit is adapted to accommodate modifications of the tri-axle if necessary or desired. Furthermore, the base unit has been described with respect to a particular battery and storage location of the battery near the base of the base module, however variations can be made to that structure as appropriate including for extended run-time where multiple batteries can be boarded. Different applications may require a different battery source and the present design easily accommodates variation in the individual components while still providing an effective platform which can be manufactured in a cost effective manner.

Although preferred embodiments of the present invention have been disclosed herein in detail, it will be understood by those skilled in the art, that variations may be made thereto without departing from the claims and the principals of the numerous inventions disclosed herein.

We claim:

1. A base module for a mobile robot comprising a base plate forming a bottom of said base module and a base shell configured to be coupled to said base plate;
   said base plate and base shell, when coupled, defining a space therebetween for housing a multi-axle having at least 3 axles, each axle coupled to an omni-wheel adjacent an outer wall of said base shell, each omni-wheel having a separate electric drive motor housed within the space and connected to an electric battery supported in the base module, wherein said omni-wheels are commonly supported by the multi-axle which is contained between said base plate and said base shell.

2. A base module for a mobile robot as claimed in claim 1 at least a portion of said base shell extends between at least two adjacent omni-wheels; said portion of said base shell configured such that when the mobile robot is tipped onto one or more of the two adjacent omni-wheels the portion of the base shell contacts the ground and one or more of said two adjacent omni-wheels cooperate with the portion of the base shell to return the mobile robot to an upright position.

3. A base module for a mobile robot as claimed in claim 2 wherein said multi-axle is a single fixed component having each of multiple axle sections connected to each other at a central point with each of said multiple axle sections extending outwardly from said central point and being located in a common plane and each axle section supports one of said omni-wheels.

4. A base module for a mobile robot as claimed in claim 3 wherein wheel hub caps do not rotate and wires can be fed through a hollow channel in the centre of each of the axle sections so that sensors or decorative elements can be affixed to the hub cap or axial flow or other hub motors installed on the stationary axle sections to drive the omni- wheels.

5. A base module for a mobile robot as claimed in claim 3 wherein said multiple axle sections are welded to each other at said central point.

6. A base module for a mobile robot as claimed in claim 1 wherein the base shell includes slots adapted to receive and retain motor plates used to secure drive motors into said base module.

7. A base module for a mobile robot as claimed in claim 1 wherein each wheel on each axle is a set of cooperating wheels.

8. A base module for a mobile robot as claimed in claim 1 wherein said base shell has a top wall having a top surface and a bottom surface, said bottom surface facing into the space; said bottom surface including mulitiple channels sized to accommodate at least part of multiple axle sections.

9. A base module for a mobile robot as claimed in claim 8 wherein said base plate has a top surface facing into the space, said top surface including mulitiple channels sized to accommodate at least part of the multiple axle sections.

10. A base module for a mobile robot as claimed in claim 9 wherein said mulitiple channels in said base plate and said mulitple channels in said base shell are configured to secure the multiple axle sections when said base plate and base shell are coupled together.

11. A base module for a mobile robot as claimed in claim 10 wherein the mulitiple channels in said base plate or the mulitple channels in said base shell include notches and corresponding tabs which fit togheter to limit movement of said multi-axle when said base plate and said base shell are coupled.

12. A base module for a mobile robot as claimed in claim 1 wherein said base plate has a top surface facing into the space, said top surface including mulitiple channels sized to accommodate at least part of multiple axle sections.

* * * * *